US012765953B2

(12) United States Patent
Ludwig et al.

(10) Patent No.: US 12,765,953 B2
(45) Date of Patent: Oct. 20, 2026

(54) SURGICAL ROBOTIC SYSTEM AND METHOD FOR USING INSTRUMENTS IN TRAINING AND SURGICAL MODES

(71) Applicant: Covidien LP, Mansfield, MA (US)

(72) Inventors: Emily M. Ludwig, New Haven, CT (US); Brian A. Rockrohr, Guilford, CT (US)

(73) Assignee: Covidien LP, Mansfield, MA (US)

( * ) Notice: Subject to any disclaimer, the term of this patent is extended or adjusted under 35 U.S.C. 154(b) by 274 days.

(21) Appl. No.: 18/383,186

(22) Filed: Oct. 24, 2023

(65) Prior Publication Data

US 2024/0138940 A1 May 2, 2024

Related U.S. Application Data

(60) Provisional application No. 63/420,154, filed on Oct. 28, 2022.

(51) Int. Cl.
*A61B 34/32* (2016.01)
*G16H 40/63* (2018.01)
*A61B 90/00* (2016.01)

(52) U.S. Cl.
CPC ............. *A61B 34/32* (2016.02); *G16H 40/63* (2018.01); *A61B 2090/066* (2016.02); *A61B 2090/0803* (2016.02)

(58) Field of Classification Search
CPC ...... A61B 2090/066; A61B 2090/0803; A61B 34/32; G16H 40/63
See application file for complete search history.

(56) References Cited

U.S. PATENT DOCUMENTS

| | | | |
|---|---|---|---|
| 6,132,368 | A | 10/2000 | Cooper |
| 6,206,903 | B1 | 3/2001 | Ramans |
| 6,246,200 | B1 | 6/2001 | Blumenkranz et al. |
| 6,312,435 | B1 | 11/2001 | Wallace et al. |
| 6,331,181 | B1 | 12/2001 | Tierney et al. |
| 6,394,998 | B1 | 5/2002 | Wallace et al. |
| 6,424,885 | B1 | 7/2002 | Niemeyer et al. |
| 6,441,577 | B2 | 8/2002 | Blumenkranz et al. |
| 6,459,926 | B1 | 10/2002 | Nowlin et al. |
| 6,491,691 | B1 | 12/2002 | Morley et al. |
| 6,491,701 | B2 | 12/2002 | Tierney et al. |
| 6,493,608 | B1 | 12/2002 | Niemeyer |
| 6,565,554 | B1 | 5/2003 | Niemeyer |
| 6,645,196 | B1 | 11/2003 | Nixon et al. |
| 6,659,939 | B2 | 12/2003 | Moll |
| 6,671,581 | B2 | 12/2003 | Niemeyer et al. |
| 6,676,684 | B1 | 1/2004 | Morley et al. |
| 6,685,698 | B2 | 2/2004 | Morley et al. |
| 6,699,235 | B2 | 3/2004 | Wallace et al. |

(Continued)

*Primary Examiner* — Michael J Carey
(74) *Attorney, Agent, or Firm* — Carter, DeLuca & Farrell, LLP

(57) ABSTRACT

A surgical robotic system includes a surgical instrument and a robotic arm having an instrument drive unit configured to couple to and to actuate the surgical instrument. The system also includes a controller configured to: access usage data pertaining the surgical instrument; select an instrument operational mode for the surgical instrument based the usage data, the instrument operational mode being one of a surgical mode or a training mode; and enable use of the surgical instrument based on the selected instrument operational mode.

16 Claims, 7 Drawing Sheets

(56) References Cited

U.S. PATENT DOCUMENTS 6,714,839 B2 3/2004 Salisbury, Jr. et al.
6,716,233 B1 4/2004 Whitman
6,728,599 B2 4/2004 Wang et al.
6,746,443 B1 6/2004 Morley et al.
6,766,204 B2 7/2004 Niemeyer et al.
6,770,081 B1 8/2004 Cooper et al.
6,772,053 B2 8/2004 Niemeyer
6,783,524 B2 8/2004 Anderson et al.
6,793,652 B1 9/2004 Whitman et al.
6,793,653 B2 9/2004 Sanchez et al.
6,799,065 B1 9/2004 Niemeyer
6,837,883 B2 1/2005 Moll et al.
6,839,612 B2 1/2005 Sanchez et al.
6,840,938 B1 1/2005 Morley et al.
6,843,403 B2 1/2005 Whitman
6,846,309 B2 1/2005 Whitman et al.
6,866,671 B2 3/2005 Tierney et al.
6,871,117 B2 3/2005 Wang et al.
6,879,880 B2 4/2005 Nowlin et al.
6,899,705 B2 5/2005 Niemeyer
6,902,560 B1 6/2005 Morley et al.
6,936,042 B2 8/2005 Wallace et al.
6,951,535 B2 10/2005 Ghodoussi et al.
6,974,449 B2 12/2005 Niemeyer
6,991,627 B2 1/2006 Madhani et al.
6,994,708 B2 2/2006 Manzo
7,048,745 B2 5/2006 Tierney et al.
7,066,926 B2 6/2006 Wallace et al.
7,118,582 B1 10/2006 Wang et al.
7,125,403 B2 10/2006 Julian et al.
7,155,315 B2 12/2006 Niemeyer et al.
7,239,940 B2 7/2007 Wang et al.
7,306,597 B2 12/2007 Manzo
7,357,774 B2 4/2008 Cooper
7,373,219 B2 5/2008 Nowlin et al.
7,379,790 B2 5/2008 Toth et al.
7,386,365 B2 6/2008 Nixon
7,391,173 B2 6/2008 Schena
7,398,707 B2 7/2008 Morley et al.
7,413,565 B2 8/2008 Wang et al.
7,453,227 B2 11/2008 Prisco et al.
7,524,320 B2 4/2009 Tierney et al.
7,574,250 B2 8/2009 Niemeyer
7,594,912 B2 9/2009 Cooper et al.
7,607,440 B2 10/2009 Coste-Maniere et al.
7,666,191 B2 2/2010 Orban, III et al.
7,682,357 B2 3/2010 Ghodoussi et al.
7,689,320 B2 3/2010 Prisco et al.
7,695,481 B2 4/2010 Wang et al.
7,695,485 B2 4/2010 Whitman et al.
7,699,855 B2 4/2010 Anderson et al.
7,713,263 B2 5/2010 Niemeyer
7,725,214 B2 5/2010 Diolaiti
7,727,244 B2 6/2010 Orban, III et al.
7,741,802 B2 6/2010 Prisco
7,756,036 B2 7/2010 Druke et al.
7,757,028 B2 7/2010 Druke et al.
7,762,825 B2 7/2010 Burbank et al.
7,778,733 B2 8/2010 Nowlin et al.
7,803,151 B2 9/2010 Whitman
7,806,891 B2 10/2010 Nowlin et al.
7,819,859 B2 10/2010 Prisco et al.
7,819,885 B2 10/2010 Cooper
7,824,401 B2 11/2010 Manzo et al.
7,835,823 B2 11/2010 Sillman et al.
7,843,158 B2 11/2010 Prisco
7,865,266 B2 1/2011 Moll et al.
7,865,269 B2 1/2011 Prisco et al.
7,886,743 B2 2/2011 Cooper et al.
7,899,578 B2 3/2011 Prisco et al.
7,907,166 B2 3/2011 Lamprecht et al.
7,935,130 B2 5/2011 Williams
7,963,913 B2 6/2011 Devengenzo et al.
7,983,793 B2 7/2011 Toth et al.
8,002,767 B2 8/2011 Sanchez
8,004,229 B2 8/2011 Nowlin et al.
8,012,170 B2 9/2011 Whitman et al.
8,054,752 B2 11/2011 Druke et al.
8,062,288 B2 11/2011 Cooper et al.
8,079,950 B2 12/2011 Stern et al.
8,100,133 B2 1/2012 Mintz et al.
8,108,072 B2 1/2012 Zhao et al.
8,120,301 B2 2/2012 Goldberg et al.
8,142,447 B2 3/2012 Cooper et al.
8,147,503 B2 4/2012 Zhao et al.
8,151,661 B2 4/2012 Schena et al.
8,155,479 B2 4/2012 Hoffman et al.
8,182,469 B2 5/2012 Anderson et al.
8,202,278 B2 6/2012 Orban, III et al.
8,206,406 B2 6/2012 Orban, III
8,210,413 B2 7/2012 Whitman et al.
8,216,250 B2 7/2012 Orban, III et al.
8,220,468 B2 7/2012 Cooper et al.
8,256,319 B2 9/2012 Cooper et al.
8,285,517 B2 10/2012 Sillman et al.
8,315,720 B2 11/2012 Mohr et al.
8,335,590 B2 12/2012 Costa et al.
8,347,757 B2 1/2013 Duval
8,374,723 B2 2/2013 Zhao et al.
8,418,073 B2 4/2013 Mohr et al.
8,419,717 B2 4/2013 Diolaiti et al.
8,423,182 B2 4/2013 Robinson et al.
8,452,447 B2 5/2013 Nixon
8,454,585 B2 6/2013 Whitman
8,499,992 B2 8/2013 Whitman et al.
8,508,173 B2 8/2013 Goldberg et al.
8,528,440 B2 9/2013 Morley et al.
8,529,582 B2 9/2013 Devengenzo et al.
8,540,748 B2 9/2013 Murphy et al.
8,551,116 B2 10/2013 Julian et al.
8,562,594 B2 10/2013 Cooper et al.
8,594,841 B2 11/2013 Zhao et al.
8,597,182 B2 12/2013 Stein et al.
8,597,280 B2 12/2013 Cooper et al.
8,600,551 B2 12/2013 Itkowitz et al.
8,608,773 B2 12/2013 Tierney et al.
8,620,473 B2 12/2013 Diolaiti et al.
8,624,537 B2 1/2014 Nowlin et al.
8,634,957 B2 1/2014 Toth et al.
8,638,056 B2 1/2014 Goldberg et al.
8,638,057 B2 1/2014 Goldberg et al.
8,644,988 B2 2/2014 Prisco et al.
8,666,544 B2 3/2014 Moll et al.
8,668,638 B2 3/2014 Donhowe et al.
8,746,252 B2 6/2014 McGrogan et al.
8,749,189 B2 6/2014 Nowlin et al.
8,749,190 B2 6/2014 Nowlin et al.
8,758,352 B2 6/2014 Cooper et al.
8,761,930 B2 6/2014 Nixon
8,768,516 B2 7/2014 Diolaiti et al.
8,786,241 B2 7/2014 Nowlin et al.
8,790,243 B2 7/2014 Cooper et al.
8,808,164 B2 8/2014 Hoffman et al.
8,816,628 B2 8/2014 Nowlin et al.
8,821,480 B2 9/2014 Burbank
8,823,308 B2 9/2014 Nowlin et al.
8,827,989 B2 9/2014 Niemeyer
8,838,270 B2 9/2014 Druke et al.
8,852,174 B2 10/2014 Burbank
8,858,547 B2 10/2014 Brogna
8,862,268 B2 10/2014 Robinson et al.
8,864,751 B2 10/2014 Prisco et al.
8,864,752 B2 10/2014 Diolaiti et al.
8,903,546 B2 12/2014 Diolaiti et al.
8,903,549 B2 12/2014 Itkowitz et al.
8,911,428 B2 12/2014 Cooper et al.
8,912,746 B2 12/2014 Reid et al.
8,944,070 B2 2/2015 Guthart
8,989,903 B2 3/2015 Weir et al.
9,002,518 B2 4/2015 Manzo
9,014,856 B2 4/2015 Manzo et al.
9,016,540 B2 4/2015 Whitman et al.
9,019,345 B2 4/2015 O'Grady et al.
9,043,027 B2 5/2015 Durant et al.

(56) References Cited

U.S. PATENT DOCUMENTS 9,050,120 B2 6/2015 Swarup et al.
9,055,961 B2 6/2015 Manzo et al.
9,068,628 B2 6/2015 Solomon et al.
9,078,684 B2 7/2015 Williams
9,084,623 B2 7/2015 Gomez et al.
9,095,362 B2 8/2015 Dachs, II et al.
9,096,033 B2 8/2015 Holop et al.
9,101,381 B2 8/2015 Burbank et al.
9,113,877 B1 8/2015 Whitman et al.
9,138,284 B2 9/2015 Krom et al.
9,144,456 B2 9/2015 Rosa et al.
9,198,730 B2 12/2015 Prisco et al.
9,204,923 B2 12/2015 Manzo et al.
9,226,648 B2 1/2016 Saadat et al.
9,226,750 B2 1/2016 Weir et al.
9,226,761 B2 1/2016 Burbank
9,232,984 B2 1/2016 Guthart et al.
9,241,766 B2 1/2016 Duque et al.
9,241,767 B2 1/2016 Prisco et al.
9,241,769 B2 1/2016 Larkin et al.
9,259,275 B2 2/2016 Burbank
9,259,277 B2 2/2016 Rogers et al.
9,259,281 B2 2/2016 Griffiths et al.
9,259,282 B2 2/2016 Azizian et al.
9,261,172 B2 2/2016 Solomon et al.
9,265,567 B2 2/2016 Orban, III et al.
9,265,584 B2 2/2016 Itkowitz et al.
9,283,049 B2 3/2016 Diolaiti et al.
9,301,811 B2 4/2016 Goldberg et al.
9,314,307 B2 4/2016 Richmond et al.
9,317,651 B2 4/2016 Nixon
9,345,546 B2 5/2016 Toth et al.
9,393,017 B2 7/2016 Flanagan et al.
9,402,689 B2 8/2016 Prisco et al.
9,417,621 B2 8/2016 Diolaiti
9,424,303 B2 8/2016 Hoffman et al.
9,433,418 B2 9/2016 Whitman et al.
9,446,517 B2 9/2016 Burns et al.
9,452,020 B2 9/2016 Griffiths et al.
9,474,569 B2 10/2016 Manzo et al.
9,480,533 B2 11/2016 Devengenzo et al.
9,503,713 B2 11/2016 Zhao et al.
9,550,300 B2 1/2017 Danitz et al.
9,554,859 B2 1/2017 Nowlin et al.
9,566,124 B2 2/2017 Prisco et al.
9,579,164 B2 2/2017 Itkowitz et al.
9,585,641 B2 3/2017 Cooper et al.
9,615,883 B2 4/2017 Schena et al.
9,623,563 B2 4/2017 Nixon
9,623,902 B2 4/2017 Griffiths et al.
9,629,520 B2 4/2017 Diolaiti
9,662,177 B2 5/2017 Weir et al.
9,664,262 B2 5/2017 Donlon et al.
9,675,354 B2 6/2017 Weir et al.
9,687,312 B2 6/2017 Dachs, II et al.
9,700,334 B2 7/2017 Hinman et al.
9,718,190 B2 8/2017 Larkin et al.
9,730,719 B2 8/2017 Brisson et al.
9,737,199 B2 8/2017 Pistor et al.
9,795,446 B2 10/2017 DiMaio et al.
9,797,484 B2 10/2017 Solomon et al.
9,801,690 B2 10/2017 Larkin et al.
9,814,530 B2 11/2017 Weir et al.
9,814,536 B2 11/2017 Goldberg et al.
9,814,537 B2 11/2017 Itkowitz et al.
9,820,823 B2 11/2017 Richmond et al.
9,827,059 B2 11/2017 Robinson et al.
9,830,371 B2 11/2017 Hoffman et al.
9,839,481 B2 12/2017 Blumenkranz et al.
9,839,487 B2 12/2017 Dachs, II
9,850,994 B2 12/2017 Schena
9,855,102 B2 1/2018 Blumenkranz
9,855,107 B2 1/2018 Labonville et al.
9,872,737 B2 1/2018 Nixon
9,877,718 B2 1/2018 Weir et al.
9,883,920 B2 2/2018 Blumenkranz
9,888,974 B2 2/2018 Niemeyer
9,895,813 B2 2/2018 Blumenkranz et al.
9,901,408 B2 2/2018 Larkin
9,918,800 B2 3/2018 Itkowitz et al.
9,943,375 B2 4/2018 Blumenkranz et al.
9,948,852 B2 4/2018 Lilagan et al.
9,949,798 B2 4/2018 Weir
9,949,802 B2 4/2018 Cooper
9,952,107 B2 4/2018 Blumenkranz et al.
9,956,044 B2 5/2018 Gomez et al.
9,980,778 B2 5/2018 Ohline et al.
10,008,017 B2 6/2018 Itkowitz et al.
10,028,793 B2 7/2018 Griffiths et al.
10,033,308 B2 7/2018 Chaghajerdi et al.
10,034,719 B2 7/2018 Richmond et al.
10,052,167 B2 8/2018 Au et al.
10,085,811 B2 10/2018 Weir et al.
10,092,165 B2 10/2018 Power
10,092,344 B2 10/2018 Mohr et al.
10,123,844 B2 11/2018 Nowlin
10,188,471 B2 1/2019 Brisson
10,201,390 B2 2/2019 Swarup et al.
10,213,202 B2 2/2019 Flanagan et al.
10,258,416 B2 4/2019 Mintz et al.
10,278,782 B2 5/2019 Jarc et al.
10,278,783 B2 5/2019 Itkowitz et al.
10,282,881 B2 5/2019 Itkowitz et al.
10,335,242 B2 7/2019 Devengenzo et al.
10,405,934 B2 9/2019 Prisco et al.
10,433,922 B2 10/2019 Itkowitz et al.
10,464,219 B2 11/2019 Robinson et al.
10,485,621 B2 11/2019 Morrissette et al.
10,500,004 B2 12/2019 Hanuschik et al.
10,500,005 B2 12/2019 Weir et al.
10,500,007 B2 12/2019 Richmond et al.
10,507,066 B2 12/2019 DiMaio et al.
10,510,267 B2 12/2019 Jarc et al.
10,524,871 B2 1/2020 Liao
10,548,459 B2 2/2020 Itkowitz et al.
10,575,909 B2 3/2020 Robinson et al.
10,592,529 B2 3/2020 Hoffman et al.
10,595,946 B2 3/2020 Nixon
10,881,469 B2 1/2021 Robinson
10,881,473 B2 1/2021 Itkowitz et al.
10,898,188 B2 1/2021 Burbank
10,898,189 B2 1/2021 McDonald, II
10,905,506 B2 2/2021 Itkowitz et al.
10,912,544 B2 2/2021 Brisson et al.
10,912,619 B2 2/2021 Jarc et al.
10,918,387 B2 2/2021 Duque et al.
10,918,449 B2 2/2021 Solomon et al.
10,932,873 B2 3/2021 Griffiths et al.
10,932,877 B2 3/2021 Devengenzo et al.
10,939,969 B2 3/2021 Swarup et al.
10,939,973 B2 3/2021 DiMaio et al.
10,952,801 B2 3/2021 Miller et al.
10,965,933 B2 3/2021 Jarc
10,966,742 B2 4/2021 Rosa et al.
10,973,517 B2 4/2021 Wixey
10,973,519 B2 4/2021 Weir et al.
10,984,567 B2 4/2021 Itkowitz et al.
10,993,773 B2 5/2021 Cooper et al.
10,993,775 B2 5/2021 Cooper et al.
11,000,331 B2 5/2021 Krom et al.
11,013,567 B2 5/2021 Wu et al.
11,020,138 B2 6/2021 Ragosta
11,020,191 B2 6/2021 Diolaiti et al.
11,020,193 B2 6/2021 Wixey et al.
11,026,755 B2 6/2021 Weir et al.
11,026,759 B2 6/2021 Donlon et al.
11,040,189 B2 6/2021 Vaders et al.
11,045,077 B2 6/2021 Stern et al.
11,045,274 B2 6/2021 Dachs, II et al.
11,058,501 B2 7/2021 Tokarchuk et al.
11,076,925 B2 8/2021 DiMaio et al.
11,090,119 B2 8/2021 Burbank
11,096,687 B2 8/2021 Flanagan et al.
11,098,803 B2 8/2021 Duque et al.

(56) References Cited

U.S. PATENT DOCUMENTS

| | | | | |
|---|---|---|---|---|
| 11,109,925 | B2 | 9/2021 | Cooper et al. | |
| 11,116,578 | B2 | 9/2021 | Hoffman et al. | |
| 11,129,683 | B2 | 9/2021 | Steger et al. | |
| 11,135,029 | B2 | 10/2021 | Suresh et al. | |
| 11,147,552 | B2 | 10/2021 | Burbank et al. | |
| 11,147,640 | B2 | 10/2021 | Jarc et al. | |
| 11,154,373 | B2 | 10/2021 | Abbott et al. | |
| 11,154,374 | B2 | 10/2021 | Hanuschik et al. | |
| 11,160,622 | B2 | 11/2021 | Goldberg et al. | |
| 11,160,625 | B2 | 11/2021 | Wixey et al. | |
| 11,161,243 | B2 | 11/2021 | Rabindran et al. | |
| 11,166,758 | B2 | 11/2021 | Mohr et al. | |
| 11,166,770 | B2 | 11/2021 | DiMaio et al. | |
| 11,166,773 | B2 | 11/2021 | Ragosta et al. | |
| 11,173,597 | B2 | 11/2021 | Rabindran et al. | |
| 11,185,378 | B2 | 11/2021 | Weir et al. | |
| 11,191,596 | B2 | 12/2021 | Thompson et al. | |
| 11,197,729 | B2 | 12/2021 | Thompson et al. | |
| 11,213,360 | B2 | 1/2022 | Hourtash et al. | |
| 11,221,863 | B2 | 1/2022 | Azizian et al. | |
| 11,234,700 | B2 | 2/2022 | Ragosta et al. | |
| 11,241,274 | B2 | 2/2022 | Vaders et al. | |
| 11,241,290 | B2 | 2/2022 | Waterbury et al. | |
| 11,259,870 | B2 | 3/2022 | DiMaio et al. | |
| 11,259,884 | B2 | 3/2022 | Burbank | |
| 11,272,993 | B2 | 3/2022 | Gomez et al. | |
| 11,272,994 | B2 | 3/2022 | Saraliev et al. | |
| 11,291,442 | B2 | 4/2022 | Wixey et al. | |
| 11,291,513 | B2 | 4/2022 | Manzo et al. | |
| 11,376,002 | B2 | 7/2022 | Shelton, IV et al. | |
| 11,376,098 | B2 | 7/2022 | Shelton, IV et al. | |
| 11,381,759 | B2 | 7/2022 | Zhao et al. | |
| 11,382,621 | B2 | 7/2022 | Scheib et al. | |
| 11,382,624 | B2 | 7/2022 | Harris et al. | |
| 11,382,625 | B2 | 7/2022 | Huitema et al. | |
| 11,382,626 | B2 | 7/2022 | Shelton, IV et al. | |
| 11,382,627 | B2 | 7/2022 | Huitema et al. | |
| 11,382,638 | B2 | 7/2022 | Harris et al. | |
| 11,382,644 | B2 | 7/2022 | Schoettgen et al. | |
| 11,389,160 | B2 | 7/2022 | Shelton, IV et al. | |
| 11,389,255 | B2 | 7/2022 | DiMaio et al. | |
| 11,399,906 | B2 | 8/2022 | Shelton, IV et al. | |
| 11,406,379 | B2 | 8/2022 | Hess et al. | |
| 11,410,259 | B2 | 8/2022 | Harris et al. | |
| 11,419,630 | B2 | 8/2022 | Yates et al. | |
| 11,424,027 | B2 | 8/2022 | Shelton, IV | |
| 11,432,888 | B2 | 9/2022 | Diolaiti et al. | |
| 11,432,893 | B2 | 9/2022 | Itkowitz et al. | |
| 11,432,895 | B2 | 9/2022 | Loh et al. | |
| 11,439,390 | B2 | 9/2022 | Patel et al. | |
| 11,439,391 | B2 | 9/2022 | Bruns et al. | |
| 11,468,791 | B2 | 10/2022 | Jarc et al. | |
| 11,471,155 | B2 | 10/2022 | Shelton, IV et al. | |
| 11,471,221 | B2 | 10/2022 | Zhao et al. | |
| 11,478,308 | B2 | 10/2022 | Hoffman et al. | |
| 11,490,977 | B2 | 11/2022 | Schena et al. | |
| 11,497,499 | B2 | 11/2022 | Shelton, IV et al. | |
| 11,504,119 | B2 | 11/2022 | Shelton, IV et al. | |
| 11,504,124 | B2 | 11/2022 | Patel et al. | |
| 11,510,743 | B2 | 11/2022 | Shelton, IV et al. | |
| 11,517,312 | B2 | 12/2022 | Wixey | |
| 11,517,325 | B2 | 12/2022 | Shelton, IV et al. | |
| 11,518,048 | B2 | 12/2022 | Saraliev et al. | |
| 11,882,217 | B1 * | 1/2024 | Sprague | A61B 34/30 |
| 2012/0150192 | A1 * | 6/2012 | Dachs, II | A61B 34/30<br>606/130 |
| 2020/0273575 | A1 * | 8/2020 | Wolf | B25J 9/1661 |
| 2020/0337790 | A1 | 10/2020 | Mumaw et al. | |

* cited by examiner

SURGICAL ROBOTIC SYSTEM AND METHOD FOR USING INSTRUMENTS IN TRAINING AND SURGICAL MODES

CROSS-REFERENCE TO RELATED APPLICATIONS

The present application claims the benefit of and priority to U.S. Provisional Patent Application Ser. No. 63/420,154, filed on Oct. 28, 2022, the entire contents of which being incorporated herein by reference.

BACKGROUND

Surgical robotic systems are currently being used in a variety of surgical procedures, including minimally invasive medical procedures. Some surgical robotic systems include a surgeon console controlling a surgical robotic arm and a surgical instrument having an end effector (e.g., forceps or grasping instrument) coupled to and actuated by the robotic arm. In operation, the robotic arm is moved to a position over a patient and then guides the surgical instrument into a small incision via a surgical port or a natural orifice of a patient to position the end effector at a work site within the patient's body. Robotic surgery is complex and requires training and/or demonstrations to new users. However, surgical instruments are expensive and have limited usability in surgical procedures making training using actual instruments expensive.

SUMMARY

Surgical instruments have stringent reliability requirements, in place to ensure patient safety. Consequently, surgical instruments with limited reuse may functionally have significant useful life remaining even after the instrument is past its clinical use expiration point. This usage data can be harnessed for other purposes, such as training and demonstration.

This disclosure focusses on these extended uses, and how an intelligent system, such as a robotically assisted surgical system can enable these additional use cases. Surgical instruments with limited reuse may be able track usage—either directly on the instrument, or through a system of which the instrument is a part. This usage tracking may be used to disable an instrument and/or prevent subsequent usage once the tracked usage exceeds a pre-determined threshold. Typically, the instrument would then be disposed of, as there would be no further use for an expired instrument.

While usage limits are critical to ensure patient safety, expired instruments may have significant usable usage remaining between when they expire and when they fail to be functionally effective. This remaining instrument usable usage can be captured for purposes other than clinical use, for example in training (such as for animal or cadaveric use), skills development (such as to practice the fundamentals of robotic surgery), or for demonstration of system functionality, etc.

This additional value can be delivered through a variety of implementations, such as toggling an indicator in the instrument memory once a usage threshold has been passed. This indicator is then used to ensure that the system only allows attachment and continued use of the instrument if the system is configured in a training or demonstration mode.

Setting the instrument into the training/demonstration mode could have additional effects, such as allowing the system to derate the instrument performance, thereby further extending the useful life of the instrument. Performance derating may include operating an instrument drive unit, and by extension the instrument at reduced clamp forces, reduced stiffness in articulation degrees of freedom, slower accelerations, etc.

According to one embodiment of the present disclosure, a surgical robotic system is disclosed. The surgical robotic system includes a surgical instrument and a robotic arm having an instrument drive unit configured to couple to and to actuate the surgical instrument. The system also includes a controller configured to: access usage data pertaining to the surgical instrument; select an instrument operational mode for the surgical instrument based the usage data, the instrument operational mode being one of a surgical mode or a training mode; and enable use of the surgical instrument based on the selected instrument operational mode.

Implementations of the above embodiment may include one or more of the following features. According to one aspect of the above embodiment, in the surgical operation mode, the controller may be further configured to fully power the instrument drive unit. In the training mode, the instrument drive unit may be partially powered. The controller may be further configured to determine whether the surgical instrument is expired based on the usage data, and prevent use of the surgical instrument in response to the determination. The controller may be further configured to update the usage data following the use of the surgical instrument in the selected instrument operational mode. The controller may be also configured to receive a system operational mode (e.g., from a user or from the system itself) which may be one of the surgical mode or the training mode. The controller may be additionally configured to enable use of the surgical instrument based on the selected instrument operational mode and the system operational mode. The usage data may include at least one of number of activations, number of uses, total force, total torque, time used, or a mode indicator.

According to another embodiment of the present disclosure, a surgical robotic system is disclosed. The surgical robotic system includes a surgical instrument and a robotic arm having an instrument drive unit configured to couple to and to actuate the surgical instrument. The system also includes a controller configured to: set a system operational mode of the robotic arm in one of a surgical mode or a demonstration mode; access usage data pertaining the surgical instrument; compare the usage data to a usage threshold corresponding to an instrument operational mode, where the instrument operational mode is one of the surgical mode or the demonstration mode; prevent use of the surgical instrument in response to the usage data being below the usage threshold; and enable use of the surgical instrument in response to the usage data being above the usage threshold and the system operational mode.

Implementations of the above embodiment may include one or more of the following features. According to one aspect of the above embodiment, in the surgical mode, the controller may be further configured to fully power the instrument drive unit. In the demonstration mode, the instrument drive unit may be partially powered. The controller may be further configured to make a determination as to whether the surgical instrument is expired based on the usage data, and prevent use of the surgical instrument in response to the determination. The controller may be also configured to update the usage data following the use of the surgical instrument. The usage data may include at least one of number of activations, number of uses, total force, total torque, time used, or a mode indicator.

According to a further embodiment of the present disclosure, a method for enabling use of a surgical instrument is disclosed. The method includes accessing usage data pertaining the surgical instrument. The usage data may include usage data of the surgical instrument. The method also includes comparing the usage data to a usage threshold corresponding to an instrument operational mode of a surgical robotic system, where the instrument operational mode is one of a surgical mode or a training mode. The method further includes preventing use of the surgical instrument in response to the usage data being below the usage threshold, and enabling operation of the surgical instrument by an instrument drive unit in response to the usage data being above the usage threshold.

Implementations of the above embodiment may include one or more of the following features. According to one aspect of the above embodiment, the method may further include operating the surgical instrument in the surgical operation mode by fully powering the instrument drive unit. The method may also include operating the surgical instrument in the training mode by partially powering the instrument drive unit. The method may additionally include making a determination as to whether the surgical instrument is expired based on the usage data, and preventing use of the surgical instrument in response to the determination. The method may additionally include updating the usage data following the use of the surgical instrument. Accessing usage data may also include reading at least one of number of activations, number of uses, total force, total torque, time used, or a mode indicator.

BRIEF DESCRIPTION OF THE DRAWINGS

Various embodiments of the present disclosure are described herein with reference to the drawings wherein.

DETAILED DESCRIPTION

Figure 1:
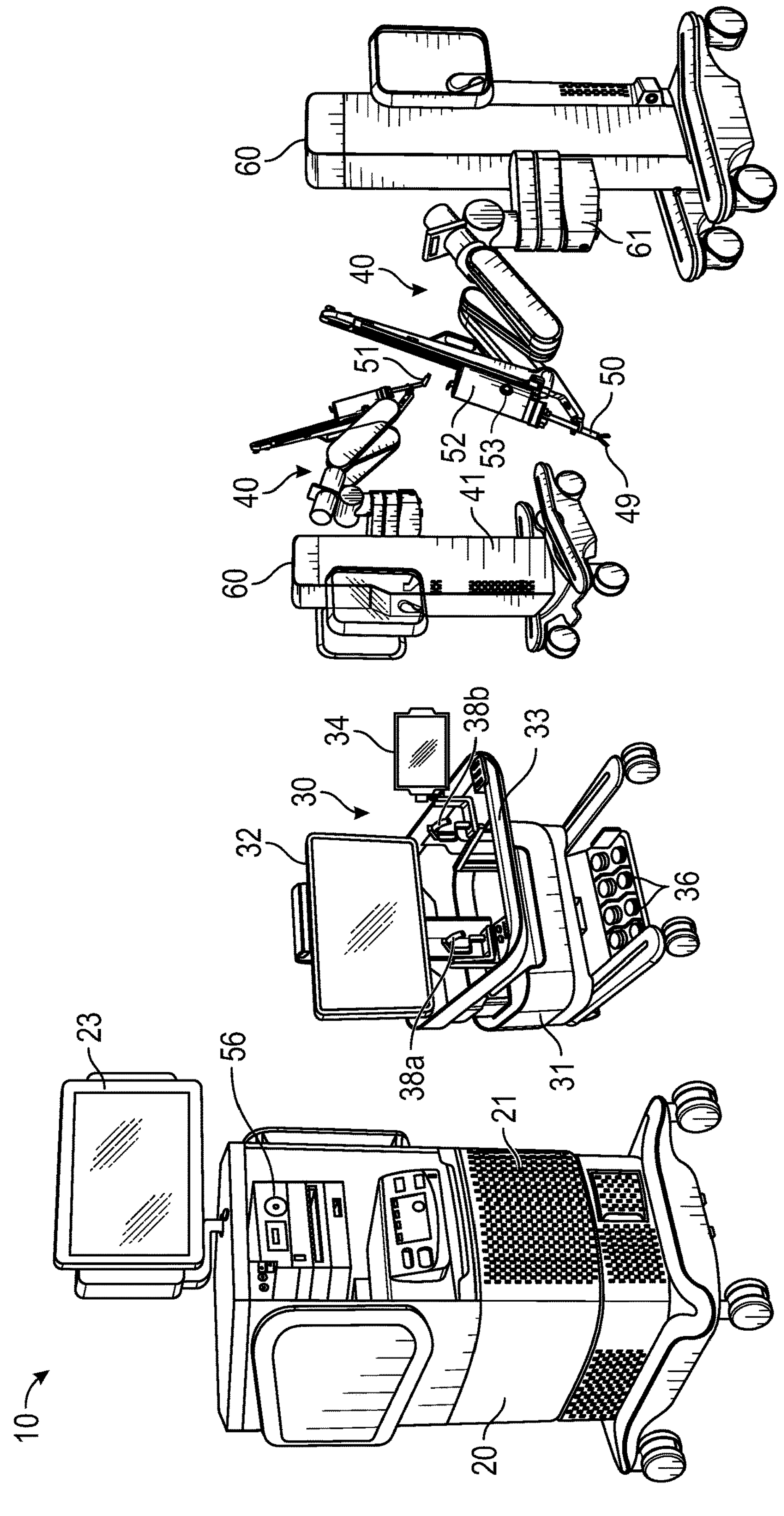
FIG. 1 is a schematic illustration of a surgical robotic system including a control tower, a console, and one or more surgical robotic arms each disposed on a movable cart according to an embodiment of the present disclosure.

Embodiments of the presently disclosed surgical robotic system are described in detail with reference to the drawings, in which like reference numerals designate identical or corresponding elements in each of the several views.

As will be described in detail below, the present disclosure is directed to a surgical robotic system, which includes a surgeon console, a control tower, and one or more movable carts having a surgical robotic arm coupled to a setup arm. The surgeon console receives user input through one or more interface devices, which are processed by the control tower as movement commands for moving the surgical robotic arm and an instrument and/or camera coupled thereto. Thus, the surgeon console enables teleoperation of the surgical arms and attached instruments/camera. The surgical robotic arm includes a controller, which is configured to process the movement command s and to generate torque commands for activating one or more actuators of the robotic arm, which would, in turn, move the robotic arm in response to the movement command.

With reference to FIG. 1, a surgical robotic system 10 includes a control tower 20, which is connected to all of the components of the surgical robotic system 10 including a surgeon console 30 and one or more movable carts 60. Each of the movable carts 60 includes a robotic arm 40 having a surgical instrument 50 removably coupled thereto. The robotic arms 40 also couple to the movable carts 60. The robotic system 10 may include any number of movable carts 60 and/or robotic arms 40.

The surgical instrument 50 is configured for use during minimally invasive surgical procedures. In embodiments, the surgical instrument 50 may be configured for open surgical procedures. In further embodiments, the surgical instrument 50 may be an electrosurgical forceps configured to seal tissue by compressing tissue between jaw members and applying electrosurgical current thereto. In yet further embodiments, the surgical instrument 50 may be a surgical stapler including a pair of jaws configured to grasp and clamp tissue while deploying a plurality of tissue fasteners, e.g., staples, and cutting stapled tissue. In yet further embodiments, the surgical instrument 50 may be a surgical clip applier including a pair of jaws configured apply a surgical clip onto tissue.

One of the robotic arms 40 may include a laparoscopic camera 51 configured to capture video of the surgical site. The laparoscopic camera 51 may be a stereoscopic endoscope configured to capture two side-by-side (i.e., left and right) images of the surgical site to produce a video stream of the surgical scene. The laparoscopic camera 51 is coupled to a image processing device 56, which may be disposed within the control tower 20. The image processing device 56 may be any computing device as described below configured to receive the video feed from the laparoscopic camera 51 and output the processed video stream.

The surgeon console 30 includes a first screen 32, which displays a video feed of the surgical site provided by camera 51 of the surgical instrument 50 disposed on the robotic arm 40, and a second screen 34, which displays a user interface for controlling the surgical robotic system 10. The first screen 32 and second screen 34 may be touchscreens allowing for displaying various graphical user inputs.

The surgeon console 30 also includes a plurality of user interface devices, such as foot pedals 36 and a pair of hand controllers *38a* and *38b* which are used by a user to remotely control robotic arms 40. The surgeon console further includes an armrest 33 used to support clinician's arms while operating the hand controllers *38a* and *38b*.

The control tower 20 includes a screen 23, which may be a touchscreen, and outputs on the graphical user interfaces (GUIs). The control tower 20 also acts as an interface between the surgeon console 30 and one or more robotic arms 40. In particular, the control tower 20 is configured to control the robotic arms 40, such as to move the robotic arms 40 and the corresponding surgical instrument 50, based on a set of programmable instructions and/or input commands from the surgeon console 30, in such a way that robotic arms 40 and the surgical instrument 50 execute a desired movement sequence in response to input from the foot pedals 36 and the hand controllers 38*a* and 38*b*. The foot pedals 36 may be used to enable and lock the hand controllers 38*a* and 38*b*, repositioning camera movement and electrosurgical activation/deactivation. In particular, the foot pedals 36 may be used to perform a clutching action on the hand controllers 38*a* and 38*b*. Clutching is initiated by pressing one of the foot pedals 36, which disconnects (i.e., prevents movement inputs) the hand controllers 38*a* and/or 38*b* from the robotic arm 40 and corresponding instrument 50 or camera 51 attached thereto. This allows the user to reposition the hand controllers 38*a* and 38*b* without moving the robotic arm(s) 40 and the instrument 50 and/or camera 51. This is useful when reaching control boundaries of the surgical space.

Each of the control tower 20, the surgeon console 30, and the robotic arm 40 includes a respective computer 21, 31, 41. The computers 21, 31, 41 are interconnected to each other using any suitable communication network based on wired or wireless communication protocols. The term "network," whether plural or singular, as used herein, denotes a data network, including, but not limited to, the Internet, Intranet, a wide area network, or a local area network, and without limitation as to the full scope of the definition of communication networks as encompassed by the present disclosure. Suitable protocols include, but are not limited to, transmission control protocol/internet protocol (TCP/IP), datagram protocol/internet protocol (UDP/IP), and/or datagram congestion control protocol (DC). Wireless communication may be achieved via one or more wireless configurations, e.g., radio frequency, optical, Wi-Fi, Bluetooth (an open wireless protocol for exchanging data over short distances, using short length radio waves, from fixed and mobile devices, creating personal area networks (PANs), ZigBee® (a specification for a suite of high level communication protocols using small, low-power digital radios based on the TREF 122.15.4-1203 standard for wireless personal area networks (WPANs)).

The computers 21, 31, 41 may include any suitable processor (not shown) operably connected to a memory (not shown), which may include one or more of volatile, non-volatile, magnetic, optical, or electrical media, such as read-only memory (ROM), random access memory (RAM), electrically-erasable programmable ROM (EEPROM), non-volatile RAM (NVRAM), or flash memory. The processor may be any suitable processor (e.g., control circuit) adapted to perform the operations, calculations, and/or set of instructions described in the present disclosure including, but not limited to, a hardware processor, a field programmable gate array (FPGA), a digital signal processor (DSP), a central processing unit (CPU), a microprocessor, and combinations thereof. Those skilled in the art will appreciate that the processor may be substituted for by using any logic processor (e.g., control circuit) adapted to execute algorithms, calculations, and/or set of instructions described herein.

Figure 2:
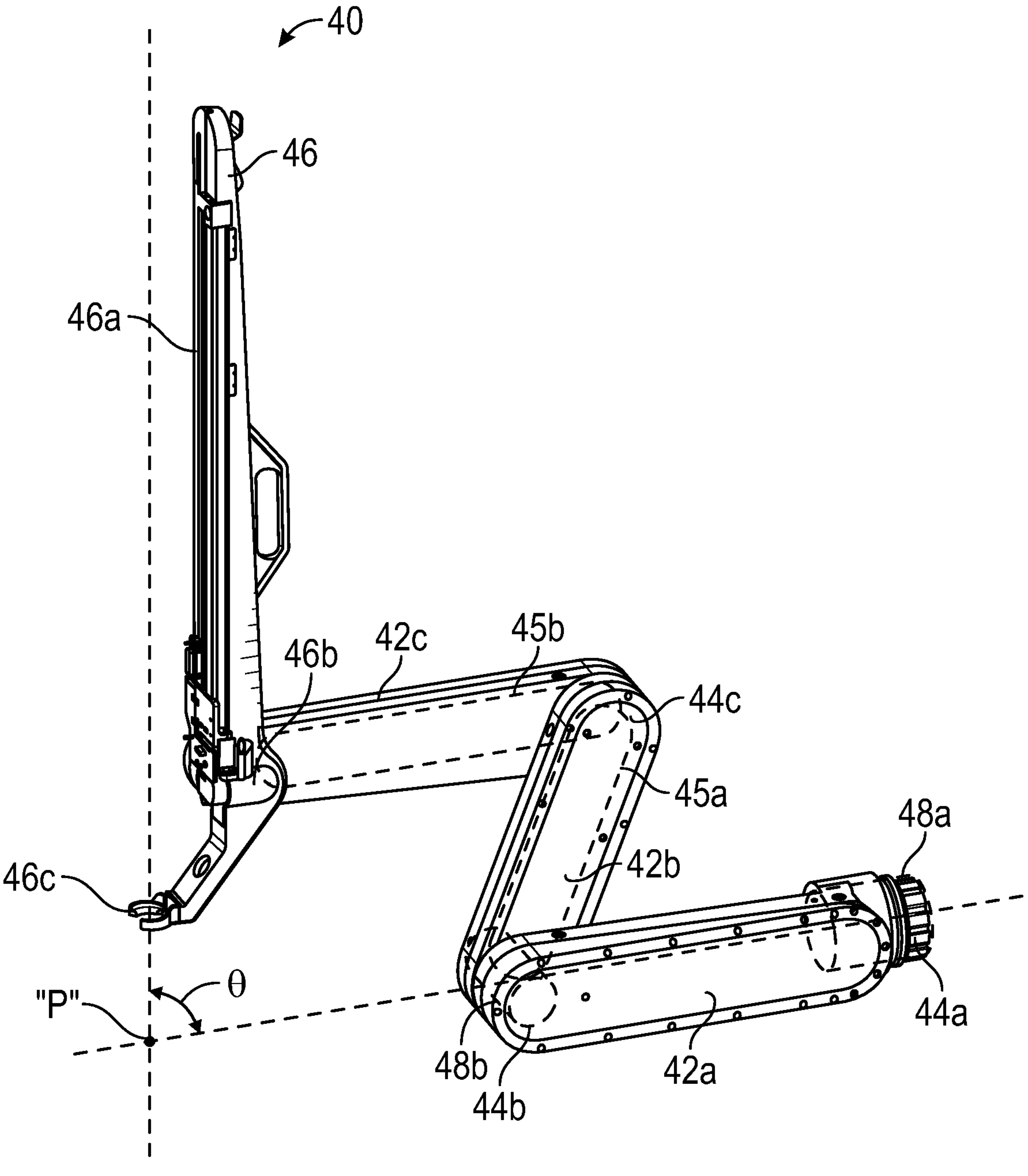
FIG. 2 is a perspective view of a surgical robotic arm of the surgical robotic system of FIG. 1 according to an embodiment of the present disclosure.
Figure 3:
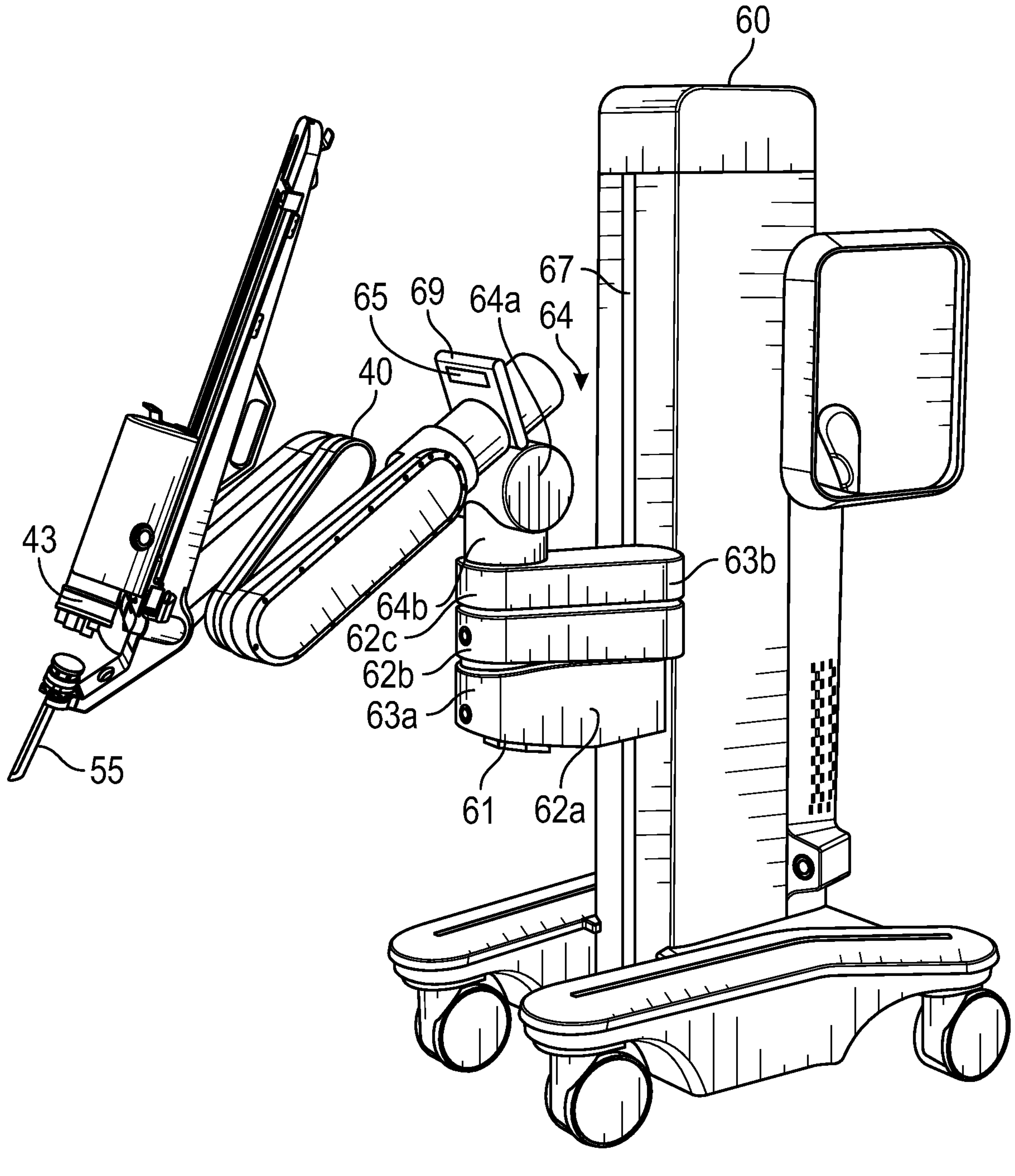
FIG. 3 is a perspective view of a movable cart having a setup arm with the surgical robotic arm of the surgical robotic system of FIG. 1 according to an embodiment of the present disclosure.

With reference to FIG. 2, each of the robotic arms 40 may include a plurality of links 42*a*, 42*b*, 42*c*, which are interconnected at joints 44*a*, 44*b*, 44*c*, respectively. Other configurations of links and joints may be utilized as known by those skilled in the art. The joint 44*a* is configured to secure the robotic arm 40 to the movable cart 60 and defines a first longitudinal axis. With reference to FIG. 3, the movable cart 60 includes a lift 67 and a setup arm 61, which provides a base for mounting of the robotic arm 40. The lift 67 allows for vertical movement of the setup arm 61. The movable cart 60 also includes a screen 69 for displaying information pertaining to the robotic arm 40. In embodiments, the robotic arm 40 may include any type and/or number of joints.

The setup arm 61 includes a first link 62*a*, a second link 62*b*, and a third link 62*c*, which provide for lateral maneuverability of the robotic arm 40. The links 62*a*, 62*b*, 62*c* are interconnected at joints 63*a* and 63*b*, each of which may include an actuator (not shown) for rotating the links 62*b* and 62*b* relative to each other and the link 62*c*. In particular, the links 62*a*, 62*b*, 62*c* are movable in their corresponding lateral planes that are parallel to each other, thereby allowing for extension of the robotic arm 40 relative to the patient (e.g., surgical table). In embodiments, the robotic arm 40 may be coupled to the surgical table (not shown). The setup arm 61 includes controls 65 for adjusting movement of the links 62*a*, 62*b*, 62*c* as well as the lift 67. In embodiments, the setup arm 61 may include any type and/or number of joints.

The third link 62*c* may include a rotatable base 64 having two degrees of freedom. In particular, the rotatable base 64 includes a first actuator 64*a* and a second actuator 64*b*. The first actuator 64*a* is rotatable about a first stationary arm axis which is perpendicular to a plane defined by the third link 62*c* and the second actuator 64*b* is rotatable about a second stationary arm axis which is transverse to the first stationary arm axis. The first and second actuators 64*a* and 64*b* allow for full three-dimensional orientation of the robotic arm 40.

The actuator 48*b* of the joint 44*b* is coupled to the joint 44*c* via the belt 45*a*, and the joint 44*c* is in turn coupled to the joint 46*b* via the belt 45*b*. Joint 44*c* may include a transfer case coupling the belts 45*a* and 45*b*, such that the actuator 48*b* is configured to rotate each of the links 42*b*, 42*c* and a holder 46 relative to each other. More specifically, links 42*b*, 42*c*, and the holder 46 are passively coupled to the actuator 48*b* which enforces rotation about a pivot point "P" which lies at an intersection of the first axis defined by the link 42*a* and the second axis defined by the holder 46. In other words, the pivot point "P" is a remote center of motion (RCM) for the robotic arm 40. Thus, the actuator 48*b* controls the angle θ between the first and second axes allowing for orientation of the surgical instrument 50. Due to the interlinking of the links 42*a*, 42*b*, 42*c*, and the holder 46 via the belts 45*a* and 45*b*, the angles between the links 42*a*, 42*b*, 42*c*, and the holder 46 are also adjusted in order to achieve the desired angle θ. In embodiments, some or all of the joints 44*a*, 44*b*, 44*c* may include an actuator to obviate the need for mechanical linkages.

The joints 44*a* and 44*b* include an actuator 48*a* and 48*b* configured to drive the joints 44*a*, 44*b*, 44*c* relative to each other through a series of belts 45*a* and 45*b* or other mechanical linkages such as a drive rod, a cable, or a lever and the like. In particular, the actuator 48*a* is configured to rotate the robotic arm 40 about a longitudinal axis defined by the link 42*a*.

With reference to FIG. 2, the holder 46 defines a second longitudinal axis and configured to receive an instrument drive unit (IDU) 52 (FIG. 1). The IDU 52 is configured to couple to an actuation mechanism of the surgical instrument 50 and the camera 51 and is configured to move (e.g., rotate) and actuate the instrument 50 and/or the camera 51. IDU 52 transfers actuation forces from its actuators to the surgical instrument 50 to actuate components an end effector 49 of the surgical instrument 50. The holder 46 includes a sliding mechanism 46*a*, which is configured to move the IDU 52 along the second longitudinal axis defined by the holder 46. The holder 46 also includes a joint 46*b*, which rotates the holder 46 relative to the link 42*c*. During endoscopic procedures, the instrument 50 may be inserted through an endoscopic access port 55 (FIG. 3) held by the holder 46. The holder 46 also includes a port latch 46*c* for securing the access port 55 to the holder 46 (FIG. 2).

The robotic arm 40 also includes a plurality of manual override buttons 53 (FIG. 1) disposed on the IDU 52 and the setup arm 61, which may be used in a manual mode. The user may press one or more of the buttons 53 to move the component associated with the button 53.

Figure 4:
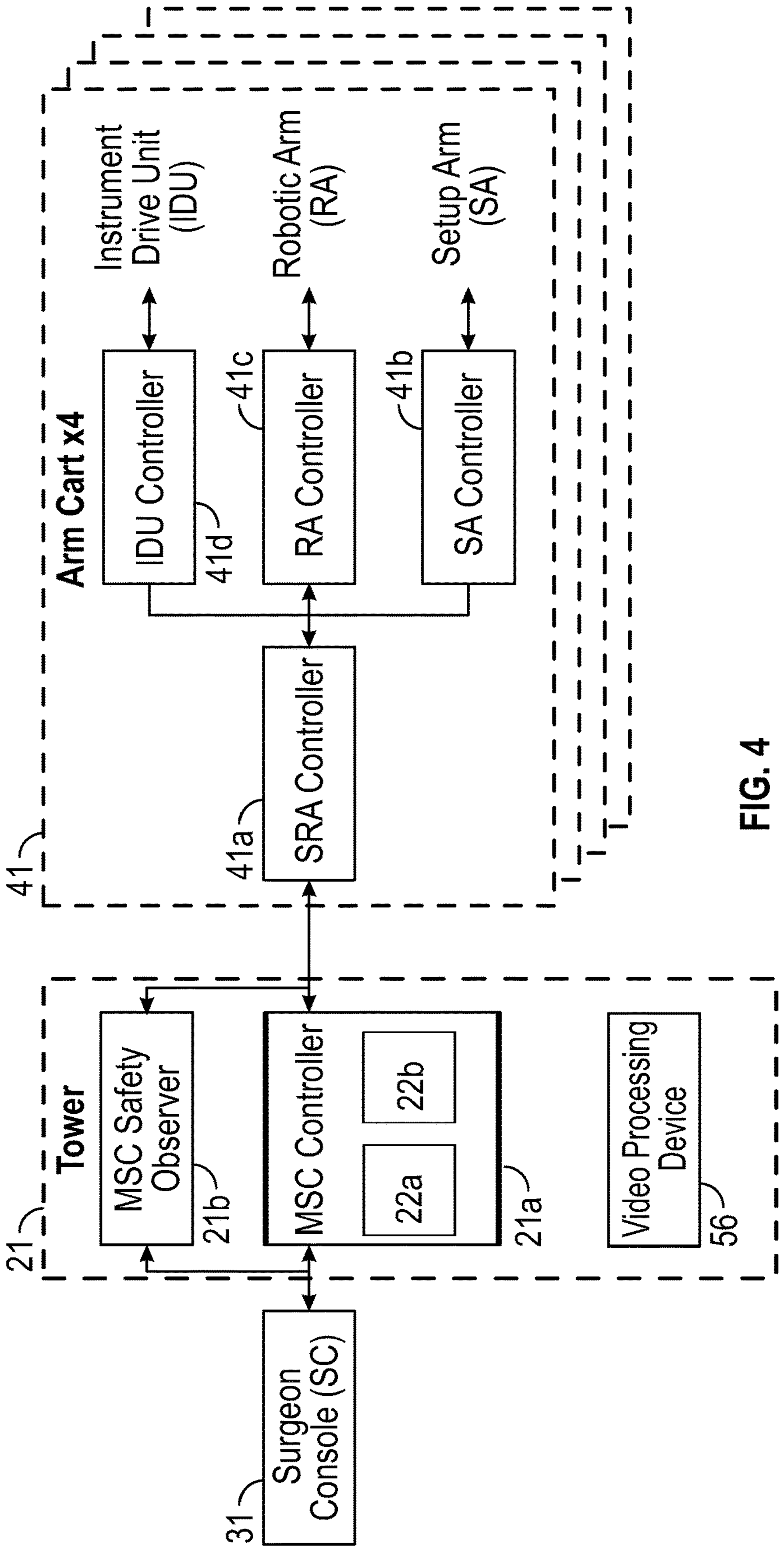
FIG. 4 is a schematic diagram of a computer architecture of the surgical robotic system of FIG. 1 according to an embodiment of the present disclosure.

With reference to FIG. 4, each of the computers 21, 31, 41 of the surgical robotic system 10 may include a plurality of controllers, which may be embodied in hardware and/or software. The computer 21 of the control tower 20 includes a controller 21*a* and safety observer 21*b*. The controller 21*a* receives data from the computer 31 of the surgeon console 30 about the current position and/or orientation of the hand controllers 38*a* and 38*b* and the state of the foot pedals 36 and other buttons. The controller 21*a* processes these input positions to determine desired drive commands for each joint of the robotic arm 40 and/or the IDU 52 and communicates these to the computer 41 of the robotic arm 40. The controller 21*a* also receives the actual joint angles measured by encoders of the actuators 48*a* and 48*b* and uses this information to determine force feedback commands that are transmitted back to the computer 31 of the surgeon console 30 to provide haptic feedback through the hand controllers 38*a* and 38*b*. The safety observer 21*b* performs validity checks on the data going into and out of the controller 21*a* and notifies a system fault handler if errors in the data transmission are detected to place the computer 21 and/or the surgical robotic system 10 into a safe state.

The controller 21*a* is coupled to a storage 22*a*, which may be non-transitory computer-readable medium configured to store any suitable computer data, such as software instructions executable by the controller 21*a*. The controller 21*a* also includes transitory memory 22*b* for loading instructions and other computer readable data during execution of the instructions. In embodiments, other controllers of the system 10 include similar configurations.

The computer 41 includes a plurality of controllers, namely, a main cart controller 41*a*, a setup arm controller 41*b*, a robotic arm controller 41*c*, and an instrument drive unit (IDU) controller 41*d*. The main cart controller 41*a* receives and processes joint commands from the controller 21*a* of the computer 21 and communicates them to the setup arm controller 41*b*, the robotic arm controller 41*c*, and the IDU controller 41*d*. The main cart controller 41*a* also manages instrument exchanges and the overall state of the movable cart 60, the robotic arm 40, and the IDU 52. The main cart controller 41*a* also communicates actual joint angles back to the controller 21*a*.

Each of joints 63*a* and 63*b* and the rotatable base 64 of the setup arm 61 are passive joints (i.e., no actuators are present therein) allowing for manual adjustment thereof by a user. The joints 63*a* and 63*b* and the rotatable base 64 include brakes that are disengaged by the user to configure the setup arm 61. The setup arm controller 41*b* monitors slippage of each of joints 63*a* and 63*b* and the rotatable base 64 of the setup arm 61, when brakes are engaged or can be freely moved by the operator when brakes are disengaged, but do not impact controls of other joints. The robotic arm controller 41*c* controls each joint 44*a* and 44*b* of the robotic arm 40 and calculates desired motor torques required for gravity compensation, friction compensation, and closed loop position control of the robotic arm 40. The robotic arm controller 41*c* calculates a movement command based on the calculated torque. The calculated motor commands are then communicated to one or more of the actuators 48*a* and 48*b* in the robotic arm 40. The actual joint positions are then transmitted by the actuators 48*a* and 48*b* back to the robotic arm controller 41*c*.

The IDU controller 41*d* receives desired joint angles for the surgical instrument 50, such as wrist and jaw angles, and computes desired currents for the motors in the IDU 52. The IDU controller 41*d* calculates actual angles based on the motor positions and transmits the actual angles back to the main cart controller 41*a*.

The robotic arm 40 is controlled in response to a pose of the hand controller controlling the robotic arm 40, e.g., the hand controller 38*a*, which is transformed into a desired pose of the robotic arm 40 through a hand eye transform function executed by the controller 21*a*. The hand eye function, as well as other functions described herein, is/are embodied in software executable by the controller 21*a* or any other suitable controller described herein. The pose of one of the hand controllers 38*a* may be embodied as a coordinate position and roll-pitch-yaw (RPY) orientation relative to a coordinate reference frame, which is fixed to the surgeon console 30. The desired pose of the instrument 50 is relative to a fixed frame on the robotic arm 40. The pose of the hand controller 38*a* is then scaled by a scaling function executed by the controller 21*a*. In embodiments, the coordinate position may be scaled down and the orientation may be scaled up by the scaling function. In addition, the controller 21*a* may also execute a clutching function, which disengages the hand controller 38*a* from the robotic arm 40. In particular, the controller 21*a* stops transmitting movement commands from the hand controller 38*a* to the robotic arm 40 if certain movement limits or other thresholds are exceeded and in essence acts like a virtual clutch mechanism, e.g., limits mechanical input from effecting mechanical output.

The desired pose of the robotic arm 40 is based on the pose of the hand controller 38*a* and is then passed by an inverse kinematics function executed by the controller 21*a*. The inverse kinematics function calculates angles for the joints 44*a*, 44*b*, 44*c* of the robotic arm 40 that achieve the scaled and adjusted pose input by the hand controller 38*a*. The calculated angles are then passed to the robotic arm controller 41*c*, which includes a joint axis controller having a proportional-derivative (PD) controller, the friction estimator module, the gravity compensator module, and a two-sided saturation block, which is configured to limit the commanded torque of the motors of the joints 44*a*, 44*b*, 44*c*.

Figure 5:
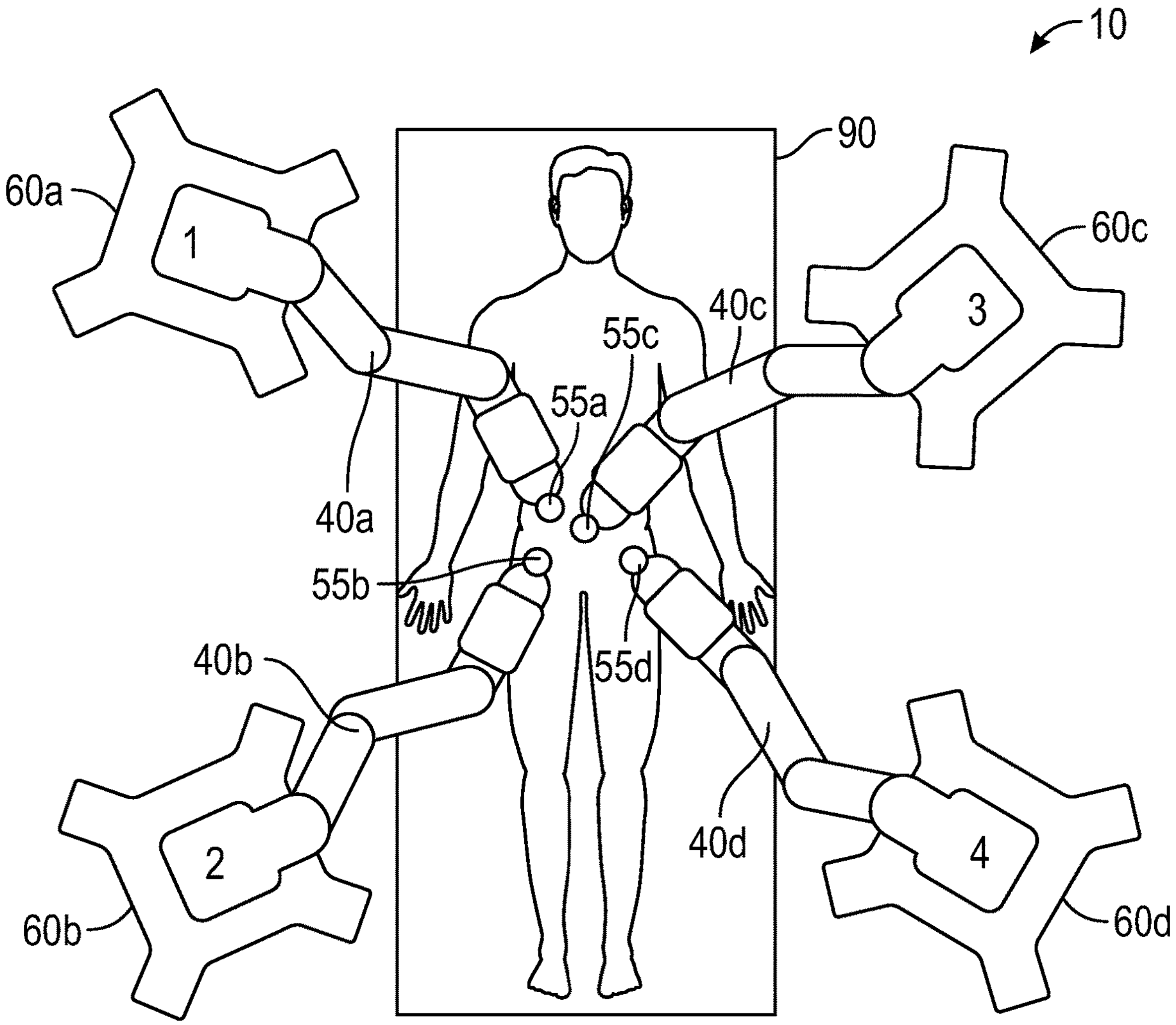
FIG. 5 is a plan schematic view of the surgical system of FIG. 1 positioned about a surgical table according to an embodiment of the present disclosure.

With reference to FIG. 5, the surgical robotic system 10 is setup around a surgical table 90. The system 10 includes movable carts 60*a-d*, which may be numbered "1" through "4." During setup, each of the carts 60*a-d* are positioned around the surgical table 90. Position and orientation of the carts 60*a-d* depends on a plurality of factors, such as placement of a plurality of access ports 55*a-d*, which in turn, depends on the surgery being performed. Once the port placement is determined, the access ports 55*a-d* are inserted into the patient, and carts 60*a-d* are positioned to insert instruments 50 and the laparoscopic camera 51 into corresponding ports 55*a-d*.

During use, each of the robotic arms 40*a-d* is attached to one of the access ports 55*a-d* that is inserted into the patient by attaching the latch 46*c* (FIG. 2) to the access port 55 (FIG. 3). The IDU 52 is attached to the holder 46, followed by the SIM 43 being attached to a distal portion of the IDU

52. Thereafter, the instrument 50 is attached to the SIM 43. The instrument 50 is then inserted through the access port 55 by moving the IDU 52 along the holder 46. The SIM 43 includes a plurality of drive shafts configured to transmit rotation of individual motors of the IDU 52 to the instrument 50 thereby actuating the instrument 50. In addition, the SIM 43 provides a sterile barrier between the instrument 50 and the other components of robotic arm 40, including the IDU 52. The SIM 43 is also configured to secure a sterile drape (not shown) to the IDU 52.

Figure 6:
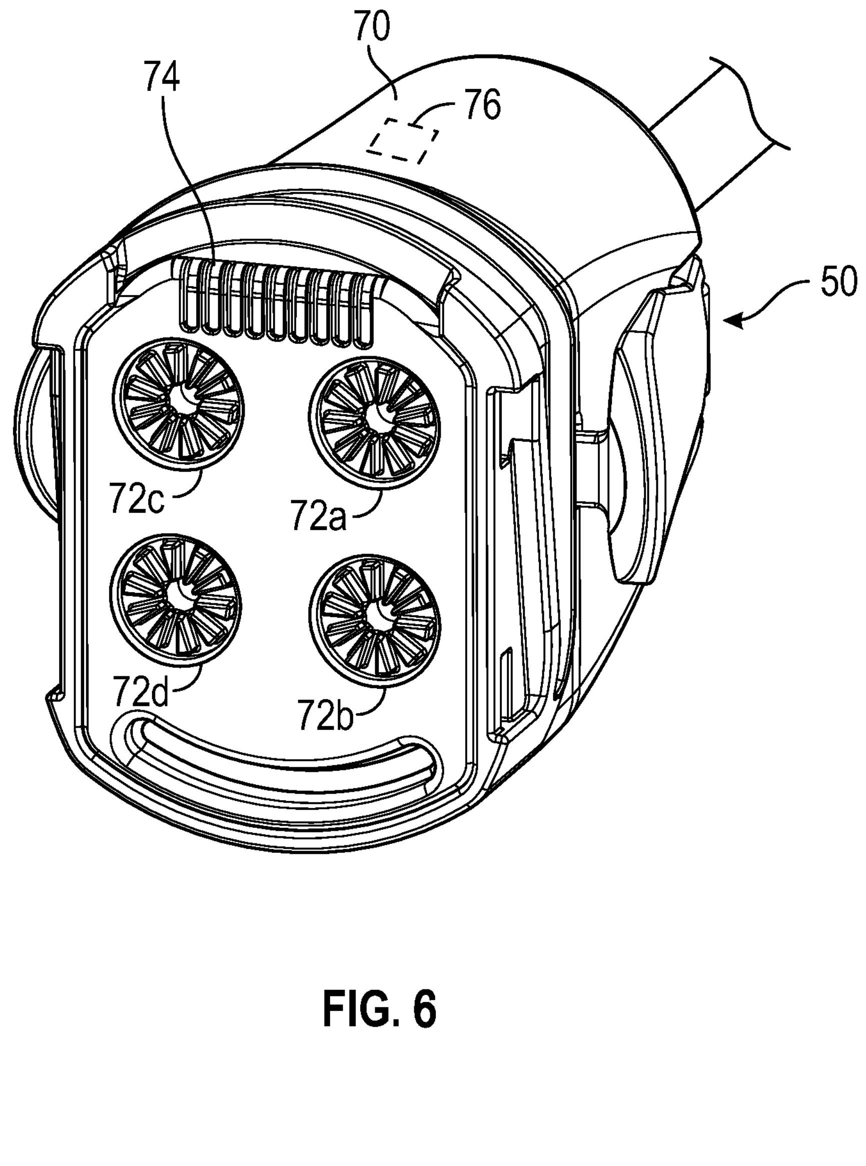
FIG. 6 is a rear perspective view of a surgical instrument according to an embodiment of the present disclosure.

With reference to FIG. 6, the instrument 50 includes a housing assembly 70 enclosing drive couplers 72*a*-*d* configured for selective connection to the IDU 52. The IDU 52 includes a plurality of motors configured to actuate each of the drive couplers 72*a*-*d* thereby actuating the instrument 50. The housing assembly 70 also includes an electrical connector 74 configured for selective connection to the IDU 52. The instrument 50 may include electronics, including, and not limited to, a memory 76, wired or wireless communication circuitry for receiving and transmitting data or information. The IDU 52 may be configured to permit passage or routing of a dedicated electrocautery cable or the like for use and connection to an electrosurgical based electromechanical surgical instrument (e.g., for ablation, coagulation, sealing, etc.).

The memory 76 may be any suitable storage device, such as flash memory and is configured to store identification information of the instrument 50, usage data, and the like. The memory 76 may be accessed by any controllers of the surgical robotic system 10, which may be the computers 21, 31, 41. In an exemplary embodiment, the main controller 21*a* is configured to read and write to the memory 76 including retrieving and updating usage data. The computers 21, 31, 41 are configured to communicate with the memory 76 through the electrical connector 74 and/or any other wired or wireless interface.

Figure 7:
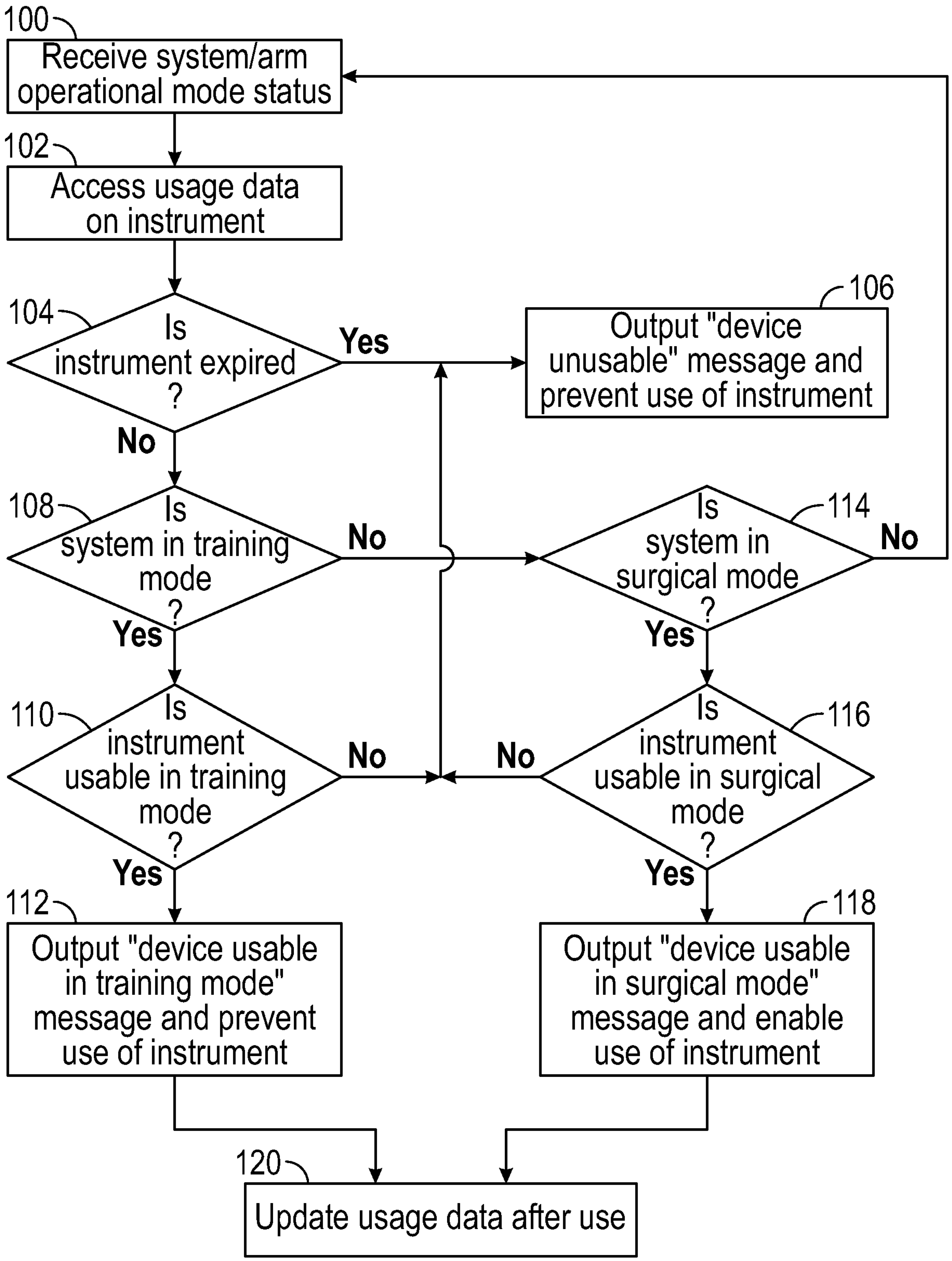
FIG. 7 is a flow chart illustrating a method for tracking useful life of instruments and enabling their use in surgical and training modes according to an embodiment of the present disclosure.

With reference to FIG. 7, a method for operating the system 10 and the instrument 50 in different operational modes is disclosed. The system 10 may be operated in a plurality of operational modes including a surgical mode and a training and/or demonstration operational mode. In the surgical mode, the system 10 is used to perform surgical procedures on a patient, whereas in a training mode (used synonymously with a demonstration, or any non-surgical mode) the system 10 is not used to perform surgical procedures on patients. Training mode may include allowing the user to manipulate the instrument 50 on a cadaver, a training implement, etc. In embodiments, rather than the system 10 switching between different modes, the system 10 may include different hardware or software versions for operating in one of the modes, i.e., surgical or training modes. The system 10 is configured to determine whether the instrument 50 is usable with the system 10 based on the usage data of the instrument 50 and depending on the operational mode of the system 10.

The method of FIG. 7 may be implemented as software instructions executable by the controller 21*a* or any other processor of the system 10. Initially, at step 100, the controller 21*a* receives the status of the operational mode to which the system 10 is set. In embodiments, the operational mode to which the system 10 is set may be the default setting, e.g., where the system 10 is configured solely for one of surgical or training use. In other embodiments, the operational mode to which the system 10 is set may be selected by a user (or another, automatic selection mechanism built into the system 10), e.g., where the system 10 is configured for operation in a plurality of modes.

For each instrument 50 that is connected to the robotic arm 40, the controller 21*a* executes the following use prediction algorithm. At step 102, the usage data from the memory 76 of the instrument 50 is accessed by the controller 21*a*. Usage data may be stored in any suitable data structure and may include the number of activations or uses, total force or torque applied, actual time used (which may be measured in seconds, minutes), etc. Use of the instrument 50 may constitute coupling the instrument 50 and activating the drive couplers 102*a*-*d* by the IDU 52. Thus, once this event occurs, the usage count is incremented by the controller 21*a*. Maximum life values may be set at the factory for each of the instruments 50.

Usage data also includes remaining life of the instrument 50. In embodiments, the main controller 21*a* may calculate the remaining life of the instrument 50 based on the usage data and display the remaining life on any of the screens 23, 32, and/or 34. In particular, the controller 21*a* may calculate remaining instrument life for the instrument 50 based on previous use of the instrument 50. The controller 21*a* may calculate remaining life as a number of uses remaining and/or a percentage of life remaining based on usage data, e.g., total minutes used vs. the total minutes allowed for the instrument 50.

In addition to usage data, the instrument 50 may also store a mode indicator indicating whether the instrument 50 is usable in a surgical mode, a training mode, or is expired and cannot be used in any mode with the system 10. Furthermore, the instrument 50 that is usable in a surgical mode, may also be enabled for use in training mode. However, the system 10, when in operating in the training mode, may be configured to operate only with instruments 50 that are no longer usable in surgical mode. This may be useful to prevent the waste of surgical instruments 50 that are usable in surgical procedures in training procedures.

At step 104, the controller 21*a* determines whether the instrument 50 is expired and is thus, unusable by the system 10 in either of the operational modes. This may be determined by comparing the usage data (e.g., time of use, number of uses, etc.) to an expiration threshold indicative of expiration of the useful life of the instrument 50. In further embodiments, the instrument 50 may include a mode indicator indicative that the instrument 50 is expired.

At step 106, after determining that the instrument 50 is expired, the controller 21*a* outputs a message on one of the screens 32, 34, etc. of the system 10 stating that the instrument 50 is expired or otherwise unusable. The controller 21*a* also prevents use of the instrument 50 by blocking any user inputs or actions that would activate or pair the instrument 50 to the IDU 52 and the system 10 at large.

After determining that the instrument 50 is not expired, the controller 21*a* proceeds with determining whether the instrument 50 is usable in one or more of the operational modes of the system 10. At step 108, the controller 21*a* determines whether the system 10 is in a training mode If so, then the controller 21*a* determines whether the instrument 50 is usable in a training mode at step 110. This may be determined by comparing the usage data to a training mode threshold or range. If the remaining useful life of the instrument is below the training mode threshold (i.e., remaining useful life is too low), then the instrument 50 is not usable and the controller 21*a* proceeds to step 106. The controller 21*a* outputs a message on one of the screens 32, 34, etc. of the system 10 stating that the instrument 50 is expired or otherwise unusable. The controller 21*a* also prevents use of the instrument 50 by blocking any user inputs or actions that would activate or pair the instrument 50 to the IDU 52 and the system 10 at large.

By way of an example, if the training mode threshold is 40% and the instrument 50 has 50% of useful life left, then the instrument 50 is useful in the training mode. Conversely, if the instrument 50 has only 30% of useful life left, then the instrument 50 is not usable in the training mode. In further embodiments, the instrument 50 may include a mode indicator indicative of whether the instrument 50 is usable in a training mode.

If the instrument 50 is usable in a training mode, then the controller 21*a* outputs a message indicating this at step 112 on any of the screens 32, 34, etc. and enables the actuation of the instrument 50 by the robotic arm 40, IDU 52, etc. In training mode, the system 10 is configured to minimize the mechanical power imparted by the instrument 50. This may include operating the IDU 52 at a lower current, lower torque thresholds, and the like.

Returning to step 108 where the controller 21*a* determines whether the system 10 is in a training mode, if the system 10 is not in a training mode, then the controller 21*a* proceeds to step 114. The controller 21*a* determines whether the system 10 is in a surgical mode, if not, then the controller 21*a* returns to step 100 to receive the current operational mode of the system 10. If the system 10 is indeed in the surgical mode, then the controller 21*a* proceeds to determine whether the instrument 50 is in fact usable in the surgical mode at step 116. In particular, the controller 21*a* compares the usage data to surgical mode threshold or range. If the remaining useful life of the instrument is below the surgical mode threshold (i.e., remaining useful life is too low), then the instrument 50 is not usable in the surgical procedure and the controller 21*a* proceeds to step 106. The controller 21*a* outputs a message on one of the screens 32, 34, etc. of the system 10 stating that the instrument 50 is not usable as requested. The controller 21*a* also prevents use of the instrument 50 by blocking any user inputs or actions that would activate or pair the instrument 50 to the IDU 52 and the system 10 at large.

By way of an example, if the surgical mode threshold is 80% and the instrument 50 has 90% of useful life left, then the instrument 50 is useful in the surgical mode. Conversely, if the instrument 50 has only 70% of useful life left, then the instrument 50 is not usable in the surgical mode. In further embodiments, the instrument 50 may include a mode indicator indicative of whether the instrument 50 is usable in a surgical mode. Thus, if the indicator indicates that the instrument 50 is usable in the selected mode, the controller 21*a* proceeds to step 118. If the instrument 50 is usable in a surgical mode, e.g., then the controller 21*a* outputs a message indicating the same at step 118 on any of the screens 32, 34, etc., and enables the actuation of the instrument 50 by the robotic arm 40, IDU 52, etc. In the surgical mode, the IDU 52 is configured to apply the full mechanical power capacity of the instrument 50.

After the instrument 50 is used in either the training mode or surgical mode, the controller 21*a*, at step 120, updates the usage data of the surgical instrument 50, e.g., increments number of activations or uses, total force or torque applied, actual time used, or toggles the mode indicator if the current use of the instrument 50 has surpassed the usage thresholds corresponding to the modes. Thus, an instrument 50 that was used in a surgical mode may still be reused in any of the modes as long as its use did not exceed the designated thresholds. Likewise the instrument 50 that is being used in the training mode, may be reused in subsequent training or demonstration uses, provided the current utilization did not surpass the expiration threshold of the instrument 50.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

What is claimed is:

1. A surgical robotic system comprising:

a surgical instrument;

a robotic arm including an instrument drive unit configured to couple to and to actuate the surgical instrument; and a controller configured to: access usage data pertaining the surgical instrument;

compare the usage data to a usage threshold corresponding to an instrument operational mode of the surgical robotic system, the instrument operational mode being one of a surgical mode or a training mode;

determine whether the surgical instrument is expired based on the usage data;

prevent use of the surgical instrument in the surgical mode in response to determining that the usage data is below the usage threshold; and enable operation of the surgical instrument in the training mode by the instrument drive unit in response to the usage data being above the usage threshold.

2. The surgical robotic system according to claim 1, wherein in the surgical mode, the controller is further configured to fully power the instrument drive unit.

3. The surgical robotic system according to claim 1, wherein in the training mode the instrument drive unit is partially powered.

4. The surgical robotic system according to claim 1, wherein the controller is further configured to update the usage data following the use of the surgical instrument.

5. The surgical robotic system according to claim 1, wherein the controller is further configured to receive a system operational mode, the system operational mode being one of the surgical mode or the training mode.

6. The surgical robotic system according to claim 1, wherein the usage data includes at least one of number of activations, number of uses, total force, total torque, time used, or a mode indicator.

7. A surgical robotic system comprising:

a surgical instrument;

a robotic arm including an instrument drive unit configured to couple to and to actuate the surgical instrument; and a controller configured to: set a system operational mode of the robotic arm in one of a surgical mode or a demonstration mode;

access usage data pertaining the surgical instrument;

compare the usage data to a usage threshold corresponding to an instrument operational mode, the instrument operational mode being one of the surgical mode or the demonstration mode;

determine whether the surgical instrument is expired based on the usage data;

prevent use of the surgical instrument in the surgical mode in response to determining that the usage data being is below the usage threshold; and enable use of the surgical instrument in the demonstration mode in response to:

the usage data being above the usage threshold, and the system operational mode corresponding to the instrument operational mode.

8. The surgical robotic system according to claim 7, wherein in the surgical mode, the controller is further configured to fully power the instrument drive unit.

9. The surgical robotic system according to claim 7, wherein in the demonstration mode the instrument drive unit is partially powered.

10. The surgical robotic system according to claim 7, wherein the controller is further configured to update the usage data following the use of the surgical instrument.

11. The surgical robotic system according to claim 7, wherein the usage data includes at least one of number of activations, number of uses, total force, total torque, time used, or a mode indicator.

12. A method for enabling use of a surgical instrument, the method comprising:

accessing usage data of the surgical instrument;

comparing the usage data to a usage threshold corresponding to an instrument operational mode of a surgical robotic system, the instrument operational mode being one of a surgical mode or a training mode;

determining whether the surgical instrument is expired based on the usage data;

preventing use of the surgical instrument in the surgical mode in response to determining that the usage data is below the usage threshold; and enabling operation of the surgical instrument in the training mode by an instrument drive unit in response to the usage data being above the usage threshold.

13. The method according to claim 12, further comprising:

operating the surgical instrument in the surgical mode by fully powering the instrument drive unit.

14. The method according to claim 12, further comprising:

operating the surgical instrument in the training mode by partially powering the instrument drive unit.

15. The method according to claim 12, further comprising:

updating the usage data following the use of the surgical instrument.

16. The method according to claim 12, wherein accessing usage data includes reading at least one of number of activations, number of uses, total force, total torque, time used, or a mode indicator.

* * * * *